United States Patent [19]

Jen

[11] Patent Number: 5,166,667
[45] Date of Patent: Nov. 24, 1992

[54] INTRAVENOUS INFUSION COUNTER AND ALARM APPARATUS

[76] Inventor: Chung H. Jen, 2-1Fl., No. 248, Sec. 4, Hsin Yi Rd., Taipei, Taiwan

[21] Appl. No.: 724,839

[22] Filed: Jul. 2, 1991

Related U.S. Application Data

[63] Continuation-in-part of Ser. No. 619,862, Nov. 29, 1990, abandoned.

[51] Int. Cl.⁵ .............................................. G08B 21/00
[52] U.S. Cl. .................................. 340/606; 340/618; 340/619; 128/DIG. 13
[58] Field of Search ............... 340/606, 618, 619, 621; 128/DIG. 13; 604/64, 65, 253; 73/293

[56] References Cited

U.S. PATENT DOCUMENTS 4,509,943  4/1985  Hanzawa ................ 128/DIG. 13 X
4,673,927  6/1987  Cianciavicchio et al. ..... 340/621 X

*Primary Examiner*—Jin F. Ng
*Assistant Examiner*—Jeffery A. Hofsass
*Attorney, Agent, or Firm*—Fitch, Even, Tabin & Flannery

[57] ABSTRACT

An intravenous infusion counter/alarm for counting the flow of drips, displaying dynamic speed of dripping, and alarming during malfunction, with at least a main body, an adjusting member which can be received by the main body in order to connect to a drip infusion tube, and a control circuit for providing a light source, light sensing unit, and control signals to detect the flow of dripping, to display the dynamic dripping speed, and to actuate an alarm when the flow deviates from a set value.

2 Claims, 9 Drawing Sheets

INTRAVENOUS INFUSION COUNTER AND ALARM APPARATUS

This is a continuation-in-part application of U.S. patent application Ser. No. 07/619,862 filed on Nov. 29, 1990 which is now abandoned.

BACKGROUND OF THE INVENTION

The invention relates to an intravenous infusion counter/alarm which quantifies the infusion flow, displays the rate of infusion, and alarms when the infusion malfunctions. The invention includes a main body, an adjusting means which can be inserted into the main body to which a drip infusion tube is attached, and a control circuit providing a light source, light sensing means, and a signal means which verifies the proper flow of infusion, and which sets off an alarm when the flow deviates significantly from a set value.

A conventional intravenous infusion set has a drip container, a drip infusion tube, and a transmitting hose extending therefrom, along with an adjusting valve to control the flow of the infusion. Conventionally no monitor is attached to the intravenous set, which displays the rate of infusion and which sets off an alarm when a malfunction is detected. Malfunctions, such as a blockage in the drip infusion tube or a loose adjusting valve, could be lethal to a patient. There is a need for a monitor on the intravenous infusion setup. At the present, the only monitors available are medical personnel, but the cost of diligent monitoring is high. Therefore, it is the purpose of the present invention to obviate the inadequacies of conventional intravenous infusion setups, providing a monitor and alarm such that medical staff time can be more efficiently utilized.

SUMMARY OF THE INVENTION

It is an object of the present invention to provide an intravenous infusion counter/alarm which displays the rate of infusion.

It is another object of the present invention to provide an intravenous infusion counter/alarm which alerts medical personnel to malfunctions of the infusion setup.

These and additional objects, if not set forth specifically herein, will be readily apparent to those skilled in the art from the detailed description provided hereunder, appropriate reference given to the accompanying drawings.

DETAILED DESCRIPTION OF THE PREFERRED EMBODIMENTS

Figure 1:
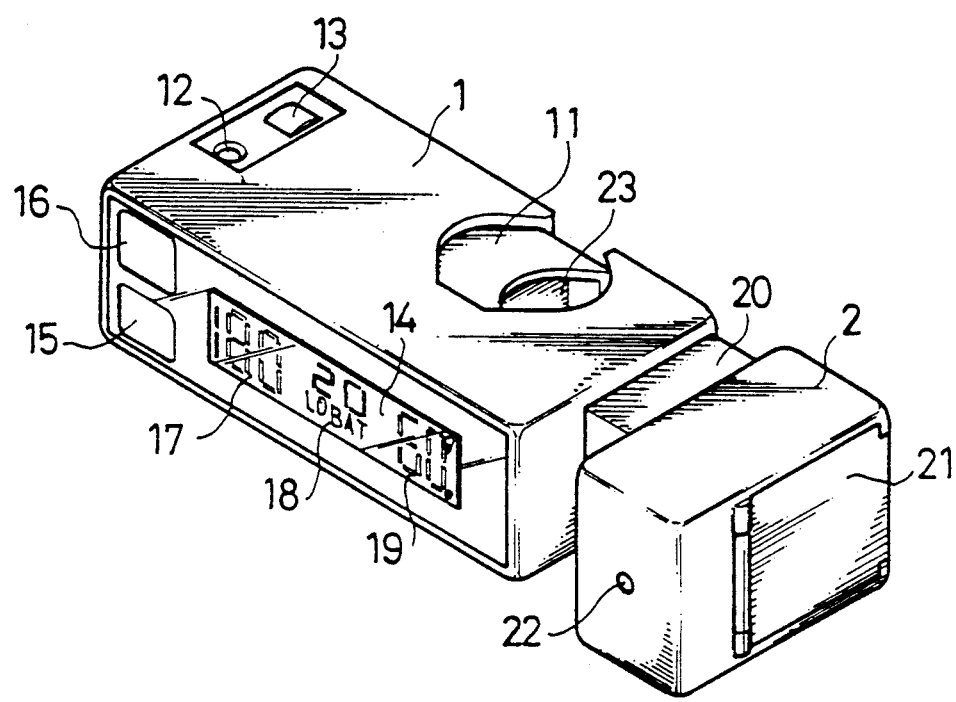
FIG. 1 is a perspective view of an intravenous infusion counter/alarm in accordance with the present invention.
Figure 2:
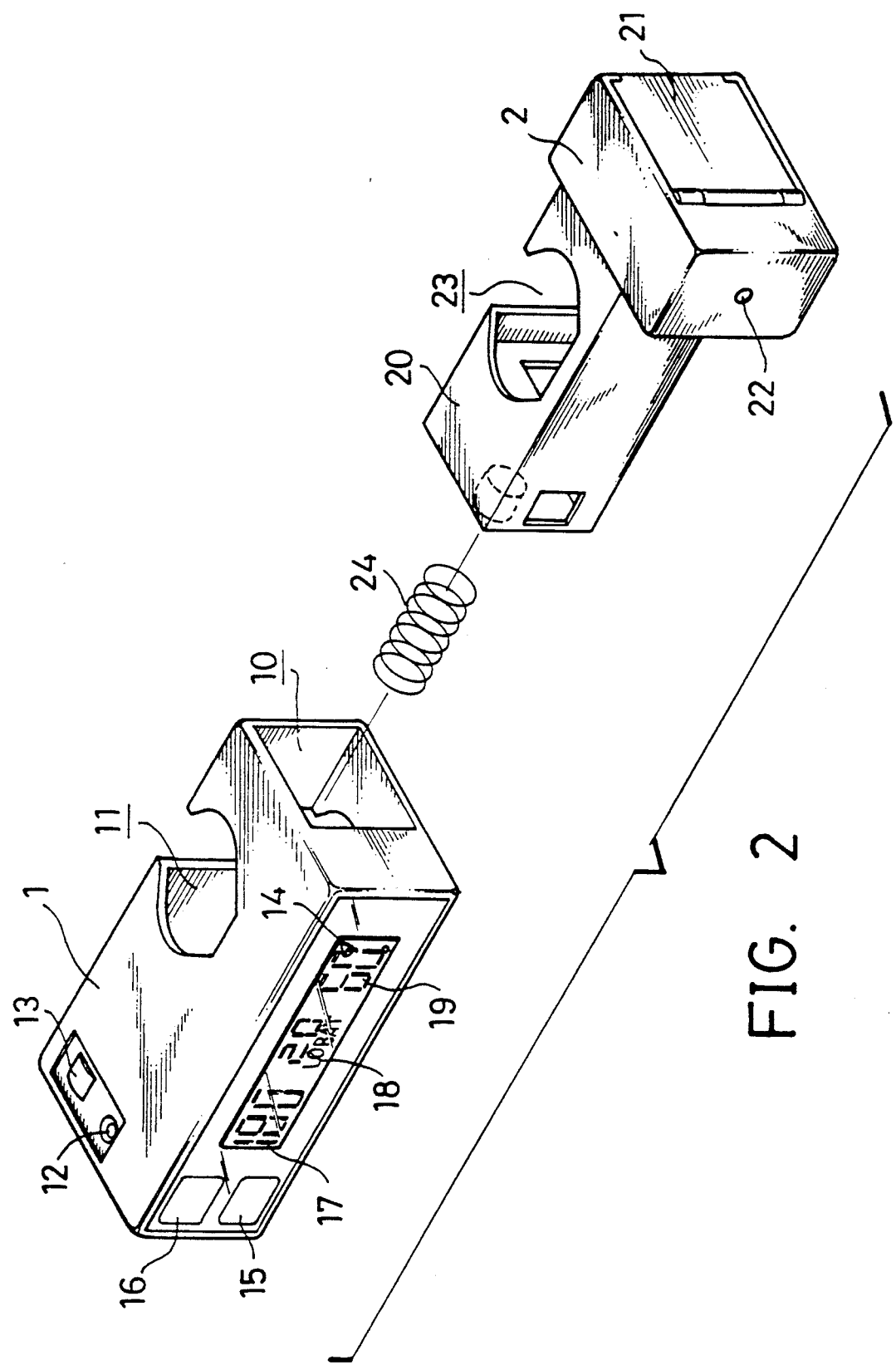
FIG. 2 is a disassembled perspective view of an intravenous infusion counter/alarm in accordance with the present invention.
Figure 3:
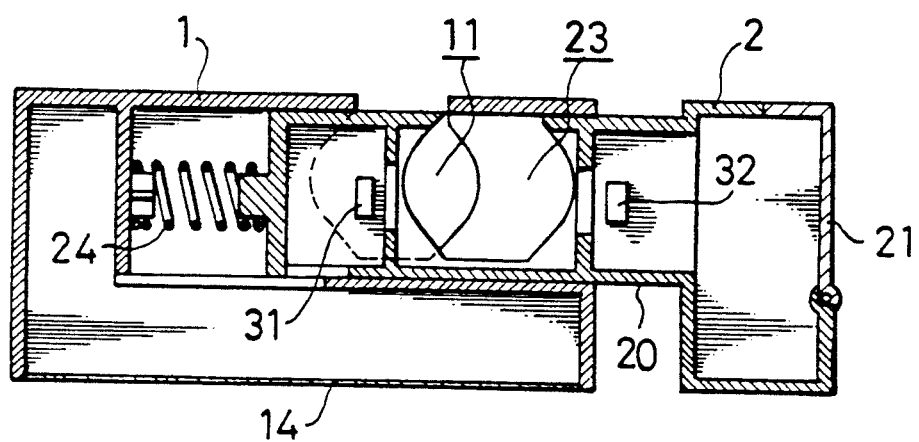
FIG. 3 is a front sectional view of an intravenous infusion counter/alarm in accordance with the present invention.
Figure 7:
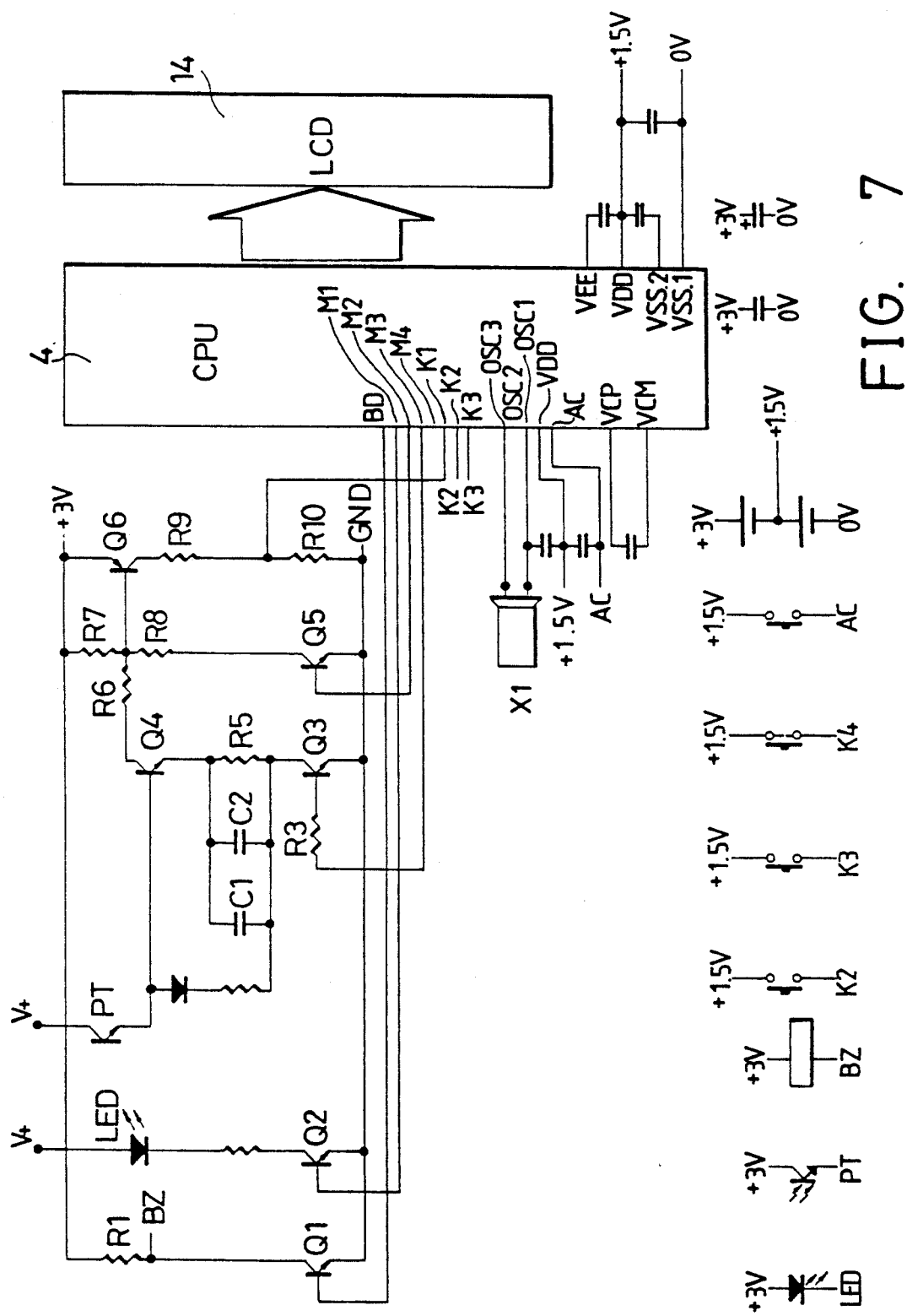
FIG. 7 is detailed circuit diagram in accordance with the present invention.
Figure 8:
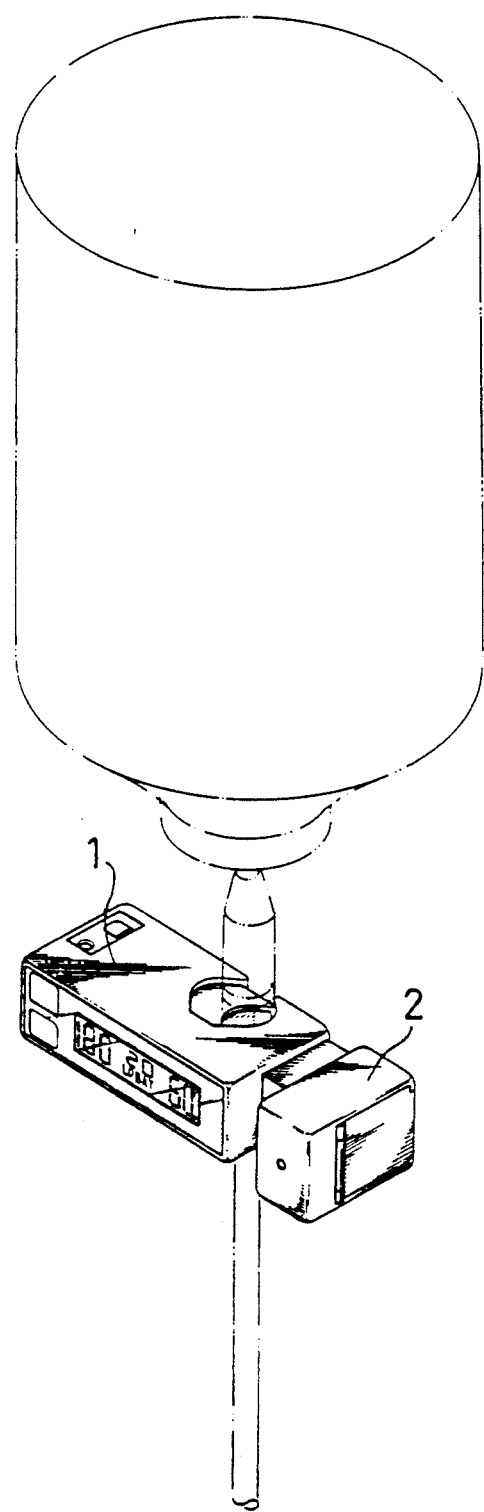
FIG. 8 is view of a preferred embodiment as it would be attached to a drip infusion tube in accordance with the present invention.
Figure 9:
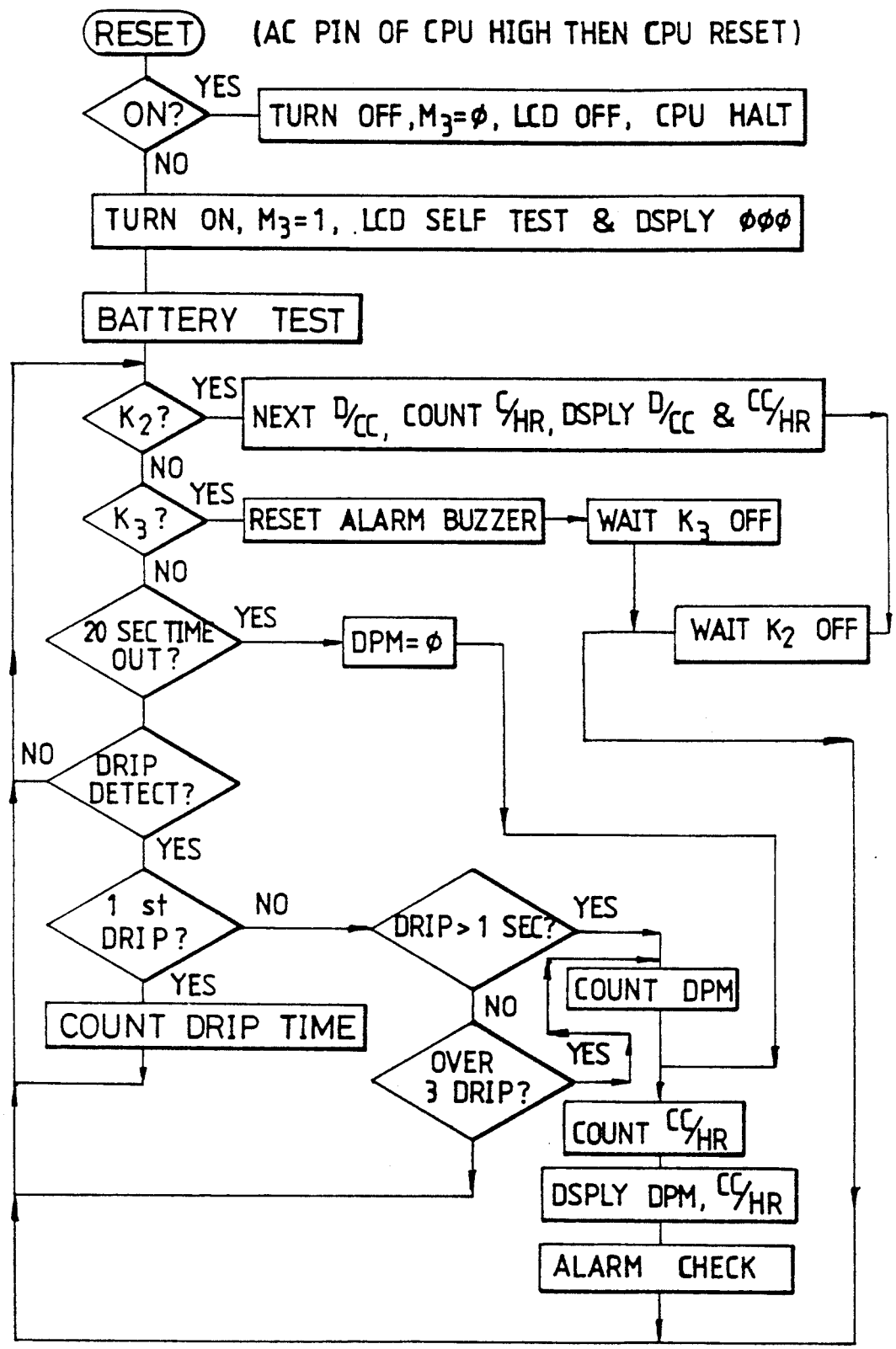
FIG. 9 is a function diagram of software for the present invention.

Referring to FIGS. 1 and 2, a preferred embodiment of an intravenous infusion counter/alarm in accordance with the present invention is illustrated as having a main body 1 and an adjusting means 2. The main body 1 has a chamber 10 for inserting the adjusting means 2, a notch 11 on an adjacent side of the main body for attaching a drip infusion tube (not included in the invention), while on the top surface of the main body 1 is an alarm reset switch 13 for shutting off an alarm 22. A reset switch 12 for resetting the whole system to start again is adjacent to the alarm reset switch 13. The front side of the main body 1 has a liquid crystal display (LCD) screen 14 showing a flow rate per hour 17, a caliber 18 of the drip infusion tube, and drips per minute 19. Adjacent to the left corner of the LCD display screen 14 is a power button 15 and a selecting switch 16. The power button 15 is used for turning power ON/OFF. The selecting switch 16 is used by an operator to generate a signal K2 which is a train of pulses to represent a volume for each drip, according to the caliber of the drip infusion tube. The signal K2 is coupled to an input port 50 of a CPU 4 (see FIG. 7), thereby setting a predetermined value in the CPU 4 for each drip.

The adjusting means 2 has a protruding body 20 inserted and extended into the chamber 10 of the main body 1, the body 20 enclosing a battery chamber 21 and an alarm 22. A notch 23 in the central part of the protruding body 20 matches the notch 11 in the main body 1. On the head of the protruding body 20 is a spring 24 which compresses against the inner wall of the chamber 10 to provide means for attaching a drip infusion tube. An LED 45 (FIG. 4) and a phototransistor 46 (FIG. 4) are disposed opposite the notch 23 of the protruding body 20. When the monitor is attached to a drip infusion tube, light from the light emitting diode (LED) passes through the drip infusion tube and reaches the phototransistor 46.

The hardware and software of the invention are further illustrated in FIGS. 4-9; a peripheral block diagram, central process unit (CPU) block diagram, drip detection timing diagram, detailed circuit schematic, and functional software flowchart, respectively.

Figure 4:
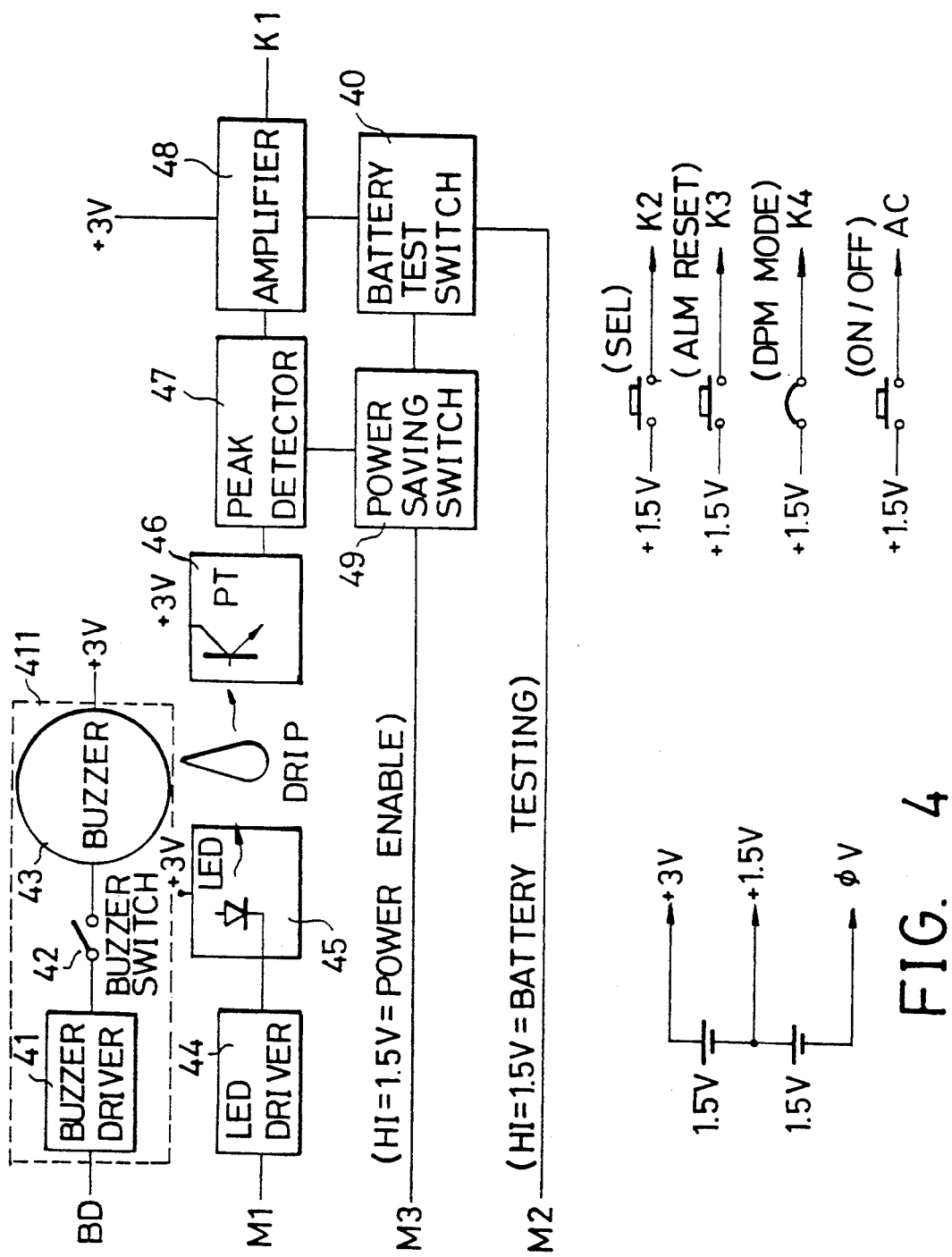
FIG. 4 is a peripheral block diagram in accordance with the present invention.

Referring to FIG. 4, a signal BD enables a buzzer driver 41, signal M1 an LED driver 44, signal M2 a battery test switch 40, and signal M3 a power saving switch 49. The LED driver 44 and battery test switch 40 are prevented by the CPU 4 from being simultaneously enabled (see FIG. 7). When signal M1 appears, the system is working in a drip detecting mode; when signal M2 appears, the system is working in a battery testing mode. Signal M3 enables a power saving switch 49 (same as $Q_3$ in FIG. 7). The LED driver 44 and the LED 45 constitute the light source for the system. The phototransistor 46 senses the light beam during operation and generates (1) a higher pulse (see FIG. 6-B, $V_A$) when the light beam reaches the phototransistor 46 without being blocked by a drip and (2) a lower pulse (see FIG. 6-B, $V_B$) when blocked.

Figure 6:
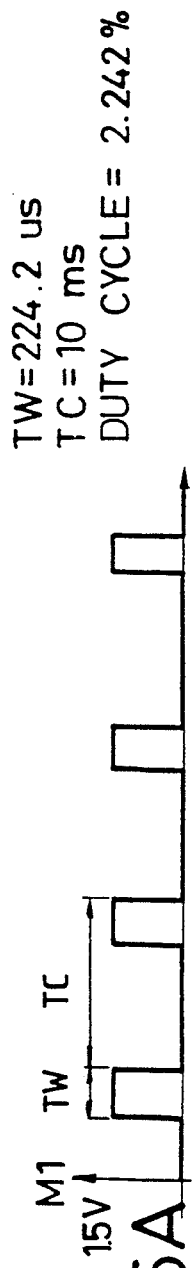
FIG. 6 including FIGS. 6-A through 6-E are drip detection timing diagrams in accordance with the present invention.
Figure 6:
Figure 6:
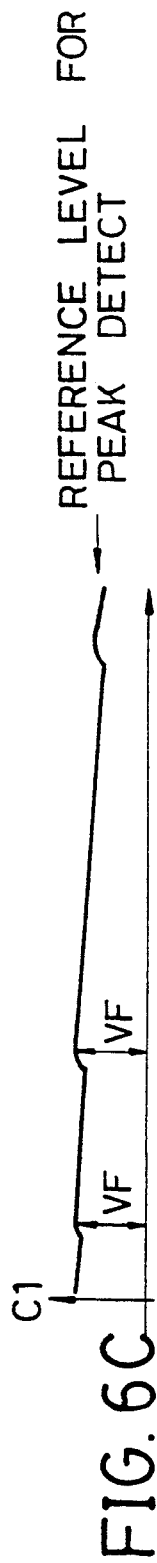
Figure 6:
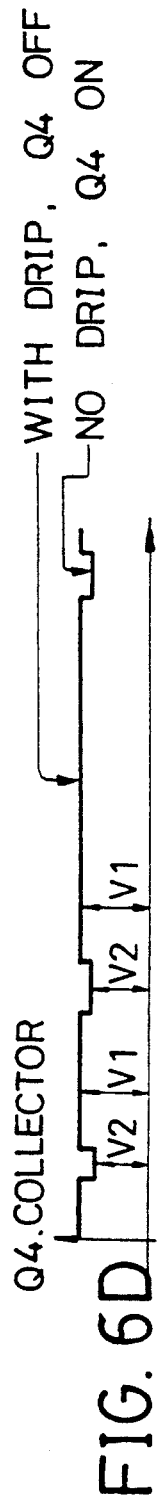
Figure 6:
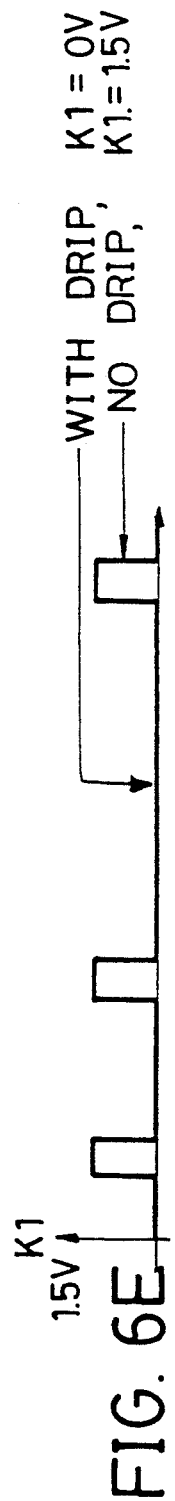

Referring to FIG. 6-C, a peak detector 47 holds a reference voltage level according to a pulse generated in the phototransistor 46. If there is no drip present, the light emitted from the LED 45 is not blocked by a drip, and the phototransistor 46 will sense a stronger light from the LED 45 and generates a higher pulse VA. If there is a drip present, the light emitted from the LED 45 will be partly blocked by the drip, and the phototransistor 46 will sense a weaker pulse VB.

The peak detector 47 includes a resistor (FIG. 7, $R_5$) and two capacitors (see FIG. 7, C1 and C2) connected in parallel. The reference voltage level is taken from the parallel capacitors $C_1$ and $C_2$. The value of the reference voltage level is established between the lower pulse level $V_B$ and the higher pulse level $V_A$ because when the phototransistor 46 generates a higher pulse VA, the capacitors C1 and C2 are charged by the higher pulse VA during a higher pulse time and then discharge to the resistor R5. When the phototransistor 46 generates a lower pulse VB, the capacitors C1 and C2 continue to discharge through the resistor R5. Therefore, the reference voltage level will be as shown in FIG. 6C.

Moreover, a transistor Q4 functions like a charging switch, that is, when the signal detected from the phototransistor 46 has the higher pulse VA which is greater than the voltage on capacitor C1 (or resistor R5), the transistor Q4 will be activated to be ON and cause a voltage of the collector thereof to be in a lower level V2; and when the signal detected from the phototransistor 46 has the lower pulse VB which is lower than the voltage on capacitor C1 (or resistor R5), the transistor Q4 will be OFF and cause a voltage of the collector thereof to be in a higher level V1, as shown in FIG. 6D.

An amplifier 48 comprising a transistor Q6 functions according to the collector voltage from transistor Q4, such that when the collector voltage of transistor Q4 has in a lower voltage V2, it causes the transistor Q6 to be ON and outputs a HIGH status of a signal K1; and when the collector voltage of transistor Q4 has in a higher voltage V1, it causes the transistor Q6 to be OFF and outputs a LOW status of the signal K1.

The buzzer means 411 for sending out an alarm beep includes a buzzer driver 41 and a buzzer 43 such that the buzzer driver 41 drives the buzzer 43 to indicate to an operator that a malfunction has occurred. A battery test switch 40 is used to test if the battery is depleted. An amplifier magnifies the current from the phototransistor 46.

The signal K1 will be sent out from the amplifier 48 in either of two cases: first, if when the system is in a drip detecting mode, it detects no drips; second, if when the system is in a battery test mode it detects the battery is OK. A power saving switch 49 is used to save unnecessary power dissipation in the phototransistor 46 by resetting the phototransistor to be OFF when the system is halted, and setting the phototransistor 46 to be On when the system is ON again. The LED driver (FIG. 7, $Q_2$) provides the LED 44 intermittent electricity.

Figure 5:
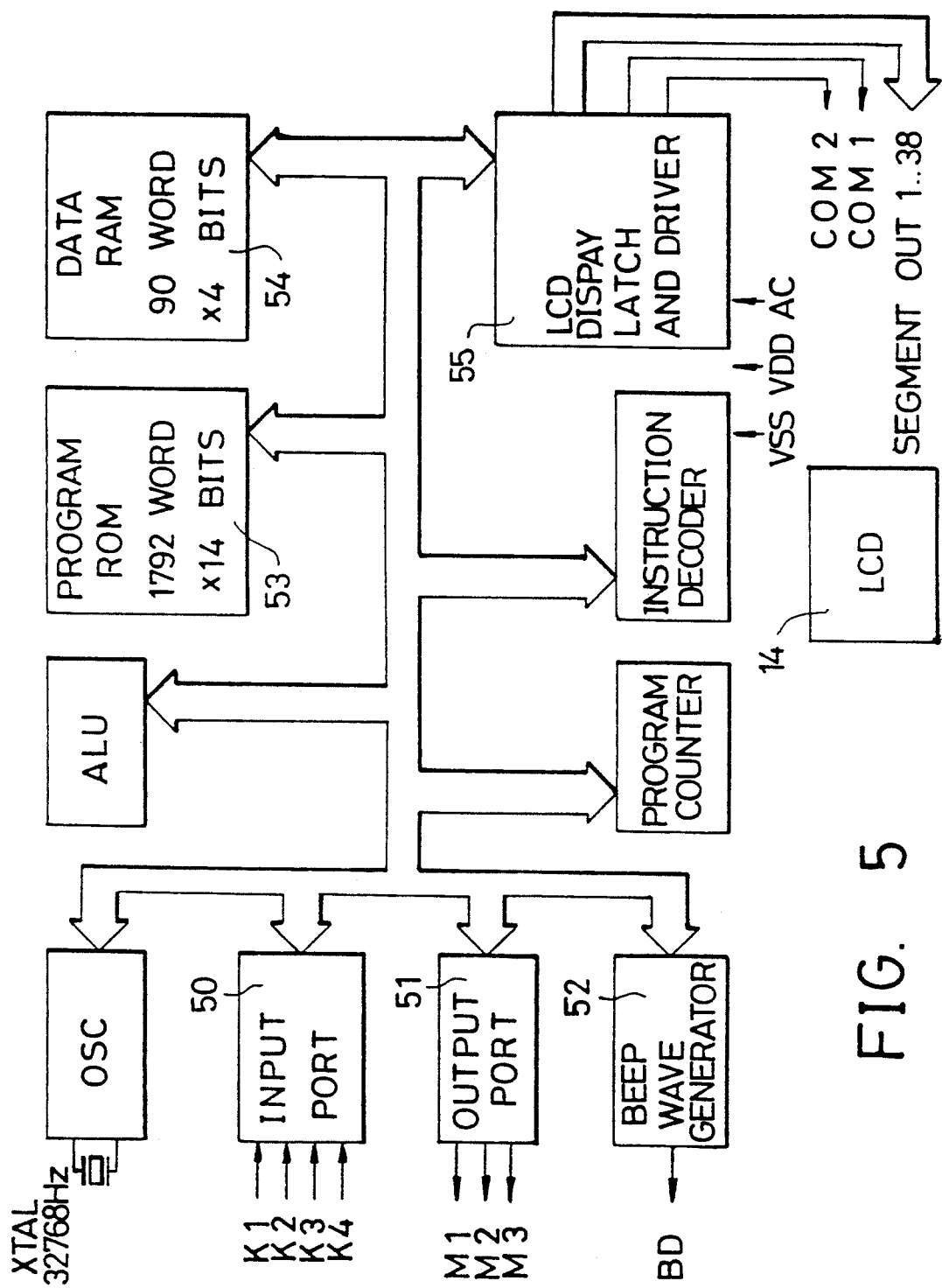
FIG. 5 is a central process unit (CPU) block diagram in accordance with the present invention.

Referring to FIG. 5, an input port 50 receives the signal K1 from the amplifier 48, a signal K2 from the selecting switch 16, and a signal K3 from the alarm reset switch 13. An LCD display latch and driver 55 controls the LCD 14 screen. Through an output port 51 is sent out any of three signals: a signal M1 which controls the LED driver 44 (FIG. 4), a signal (M2) which controls the battery test switch Q5 (FIG. 7) or a signal (M3) which controls the power saving switch 49.

A beep wave generator 52 provides a signal (BD) to control the buzzer driver 41 such that a HIGH status of the signal will actuate the buzzer driver 41 and, in turn, drives the buzzer 43. A software program is stored in a program read-only memory (ROM) 53 to run the CPU 4 to control the signals K1, K2, K3, M1, M2, M3, and BD.

While the present invention has been explained in relation to its preferred embodiment, it is to be understood that various modifications thereof will be apparent to those skilled in the art upon reading this specification. Therefore, it is to be understood that the invention disclosed herein is intended to cover all such modifications as fall within the scope of the appended claims.

I claim:

1. An intravenous infusion counter/alarm comprising a mechanical part and an electrical part, said mechanical part comprising:
   (a) a main body having
      (i) a chamber;
      (ii) a notch in one side of the main body to enable attachment onto a drip infusion tube;
      (iii) an alarm reset switch on the top surface of said main body for shutting off the alarm by sending out a signal (K3);
      (iv) a buzzer switch for allowing an operator to reset a buzzer if a malfunction occurs;
      (v) a liquid crystal display (LCD) screen showing a flow rate, a caliber of a drip infusion tube, and a drip rate;
      (vi) a power button for turning power on and off; and
      (vii) a selecting switch for sending out a signal (K2) to set volume per drip according to the caliber of said drip infusion tube; and
   (b) an adjusting means received in said main body, said adjusting means having:
      (i) a battery chamber for receiving a battery;
      (ii) a buzzer for alarming the operator if a malfunction occurs;
      (iii) a protruding body extending therefrom into the chamber of said main body;
      (iv) a notch disposed thereon which matches the notch in said main body;
      (v) a spring which is in the head of the protruding body compressing against the inner wall of said chamber;
      (vi) a light emitting diode (LED) and a phototransistor being disposed on opposing sides of said notch of said protruding body, such that when said LED is ON, said phototransistor is triggered by a light signal from said LED, and when said LED is OFF, said phototransistor is OFF; and
   said electrical part comprising:
   (a) a light beam source including an LED driver and said LED;
   (b) said phototransistor for sensing the light beam during operation and generating a higher voltage pulse when the light beam reaches said phototransistor without blockage of a drip from the intravenous infusion tube and a lower voltage pulse when blocked;
   (c) a peak detector coupled to receive said lower/higher pulse from said phototransistor and charged to a first voltage level during said higher pulse interval and then discharged to ground during a no-pulse interval, continuing to discharge to ground during said lower pulse interval and a following no-pulse interval; said charging and discharging continuing alternately and generating a reference voltage between said lower pulse level and said higher pulse level;

(d) a battery test switch for testing if said battery is depleted;

(e) an amplifier for magnifying current from said phototransistor and sending out a signal K1 showing either the absence of infusion or an adequately charged battery;

(f) a power saving switch for saving power in the phototransistors by resetting the phototransistor to be OFF when the system is halted, and setting the phototransistor to be ON when the system is ON again;

(g) an input port for receiving sid K1 signal from said amplifier, said K2 signal from said select switch, or said K3 signal from said alarm reset switch;

(h) an output port for sending out a first signal (M1) to control said power saving switch, a second signal (M2) to control said battery test switch, or a third signal (M3) to control said phototransistor;

(i) a buzzer means for sending out an alarm beep, said buzzer means including a buzzer driver and a buzzer, such that said buzzer driver drives said buzzer to indicate to an operator that a malfunction occurs;

(j) a beep wave generator providing a signal (BD) to control said buzzer driver, such that a HIGH status of said signal (BD) will actuate said buzzer driver and, in turn, drive said buzzer to alarm, and when said signal (BD) is LOW, said buzzer driver is OFF and said buzzer does not alarm;

(k) an LCD display latch and driver for controlling said LCD screen;

(l) a program read-only memory (ROM) for storing a software program which runs a central processing unit (CPU) to process said signals (K1, K2, K3, M1, M2, M3, and BD).

2. The intravenous infusion counter/alarm as claimed in claim 1, wherein said peak detector includes a switch transistor connected in series with a parallel combination of a resistor and two capacitors, such that when said phototransistor outputs a higher pulse, said switch transistor will be ON and cause said capacitors to be charged to a voltage lower than said higher pulse; when said higher pulse passes, said switch transistor will be OFF and cause said capacitors to discharge through said resistor to ground; and when said phototransistor outputs a lower pulse, said switch transistor will be OFF and cause said capacitor to continue to discharge through said resistor to ground; and when said lower pulse passes, said capacitors continue to discharge.

* * * * *